US012758474B2

(12) United States Patent
Lartigue et al.

(10) Patent No.: US 12,758,474 B2
(45) Date of Patent: Oct. 13, 2026

(54) HYDRO-ALCOHOLIC COMPOSITION FOR HAND DISINFECTION

(71) Applicant: SOCIÉTÉ D'EXPLOITATION DE PRODUITS POUR LES INDUSTRIES CHIMIQUES-SEPPIC, Paris (FR)

(72) Inventors: Marlène Lartigue, Castres (FR); Cindy Sourdon, Castres (FR); Paul Ching, Newark, DE (US); Harrison Fekrat, Newark, DE (US); Carla Perez, Paris (FR); Grace Sun, Paris (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 664 days.

(21) Appl. No.: 18/015,456

(22) PCT Filed: Jul. 1, 2021

(86) PCT No.: PCT/EP2021/068173

§ 371 (c)(1),
(2) Date: Jan. 10, 2023

(87) PCT Pub. No.: WO2022/012948

PCT Pub. Date: Jan. 20, 2022

(65) Prior Publication Data

US 2023/0329986 A1 Oct. 19, 2023

(30) Foreign Application Priority Data

Jul. 15, 2020 (FR) ....................................... 2007396

(51) Int. Cl.

| | |
|---|---|
| ***A61K 8/00*** | (2006.01) |
| ***A61K 8/06*** | (2006.01) |
| ***A61K 8/34*** | (2006.01) |
| ***A61K 8/81*** | (2006.01) |
| ***A61Q 17/00*** | (2006.01) |

(52) U.S. Cl.

CPC ................ *A61K 8/34* (2013.01); *A61K 8/066* (2013.01); *A61K 8/345* (2013.01); *A61K 8/8158* (2013.01); *A61Q 17/005* (2013.01); *A61K 2800/28* (2013.01)

(58) Field of Classification Search

None

See application file for complete search history.

(56) References Cited

U.S. PATENT DOCUMENTS

| | | | | |
|---|---|---|---|---|
| 2,798,053 | A | 7/1957 | Brown | |
| 4,956,170 | A | 9/1990 | Lee | |
| 5,373,044 | A | 12/1994 | Adams et al. | |
| 2003/0235547 | A1 | 12/2003 | Braun et al. | |
| 2007/0219315 | A1 | 9/2007 | Braun | |
| 2010/0278763 | A1 * | 11/2010 | Loeffler | A61Q 19/02 424/59 |
| 2019/0053989 | A1 * | 2/2019 | Yoon | A61K 47/32 |
| 2019/0054002 | A1 * | 2/2019 | Yoon | A61K 8/042 |
| 2020/0022934 | A1 * | 1/2020 | Mathur | A61K 9/124 |

FOREIGN PATENT DOCUMENTS

| | | | |
|---|---|---|---|
| CN | 102892823 | A | 1/2013 |
| CN | 104173248 | | 12/2014 |
| CN | 110613671 | | 12/2019 |
| EP | 0301532 | A2 | 2/1989 |
| EP | 1116733 | B1 | 4/2003 |
| EP | 0816403 | B1 | 5/2004 |
| EP | 1496081 | A1 | 1/2005 |
| EP | 1069142 | B1 | 4/2010 |
| JP | 2004059919 | A | 2/2004 |
| JP | 2011046718 | A | 3/2011 |
| JP | 2012224598 | A | 11/2012 |
| KR | 10-2100646 | | 5/2020 |
| WO | 2011030044 | A1 | 3/2011 |

OTHER PUBLICATIONS

International Search Report for PCT/EP2021/068173, mailed Oct. 6, 2021, 4 pages.

Written Opinion of the ISA for PCT/EP2021/068173, mailed Oct. 6, 2021, 8 pages.

Office Action, issued in Japanese Patent Application No. 2023-501660 dated Oct. 28, 2025.

Donald Voet and Judith G. Voet, "Biochemistry," John Wiley & Sons, 1990, p. 250.

Office Action, issued in Chinese Patent Application No. 202180060755.9 dated Nov. 5, 2024.

Search Report, issued in French Patent Application No. FR2007396 dated Apr. 1, 2021.

* cited by examiner

*Primary Examiner* — Necholus Ogden, Jr.

(74) *Attorney, Agent, or Firm* — NIXON & VANDERHYE

(57) ABSTRACT

Disclosed is a composition for disinfecting the hands, including: a) at least one alcohol including from one to four carbon atoms, b) at least one water-in-oil emulsion containing: —a crosslinked anionic polyelectrolyte (P); —a fatty phase consisting of at least one oil (H), —water, —a water-in-oil emulsifying system ($S_1$), and —an oil-in-water emulsifying system ($S_2$); c) at least one compound of formula (II): $R_2—(C{=}O)—O—(CH_2—CH_2—O)_x—CH_2—CH[(O—CH_2—CH_2)_y—O—(C{=}O)—R_3]—CH_2—(O—CH_2—CH_2)_z—O—(C{=}O)—R_4$ (II), wherein $R_2—(C{=}O)$, $R_3—(C{=}O)$ and $R_4—(C{=}O)$, identical or different, represent a saturated or unsaturated, linear or branched acyl group including from 16 to 24 carbon atoms, and wherein the sum x+y+z is greater than or equal to 30 and less than or equal to 100; and d) water.

20 Claims, No Drawings

HYDRO-ALCOHOLIC COMPOSITION FOR HAND DISINFECTION

This application is the U.S. national phase of International Application No. PCT/EP2021/068173 filed Jul. 1, 2021, which designated the U.S. and claims priority to FR Patent Application No. 2007396 filed Jul. 15, 2020, the entire contents of each of which are hereby incorporated by reference.

BACKGROUND OF THE INVENTION

Field of the Invention

A subject matter of the invention is stable and transparent hydro-alcoholic compositions, and also a method for hand disinfection employing these novel hydro-alcoholic compositions and containers comprising said novel hydro-alcoholic compositions.

Description of the Related Art

The control of nosocomial infections and exposure to infectious diseases is a concern for all medical personnel, doctors, surgeons, nurses, cleaning staff, who work both in hospitals and in ambulatory conditions.

With the development of epidemics and pandemics on the scale of an agglomeration, a country and the entire planet, this concern is also shared by operators of means of public transport (rail, river, sea or air), by managers of establishments open to the public, and by all users and inhabitants of the planet.

Disinfectant hand washing is one of the most effective means of prevention against viral, bacterial and microbial infections. It is carried out before and after contact with a patient, or with a person carrying the infection, or with a contaminated solid surface.

Disinfectant hand washing is carried out using disinfectant soap and water. These soaps can be provided in a solid form or a liquid form, and generally comprise antimicrobial agents, surface-active agents and human skin moisturizing ingredients.

The term "antimicrobial agent" denotes, within the meaning of the present invention, a family of substances which kill (microbiocidal agents) or slow down the growth (microbiostatic agents) of microbes, such as bacteria (antibacterial activity), fungi (antifungal activity), viruses (antiviral activity) or parasites (antiparasitic activity).

The term "antiseptic agent" denotes, within the meaning of the present invention, an antimicrobial agent which acts on the external surfaces of the body and more particularly on the surface of the skin.

The term "disinfection" denotes, within the meaning of the present invention, an operation of intentional and short-lived elimination of certain germs, so as to halt or prevent a microbial infection.

Mention may be made, among the most commonly used antiseptic agents, of compounds of the biguanide family, such as, for example, chlorhexidine, iodine derivatives, such as, for example, povidone-iodine, chlorinated derivatives, such as, for example, sodium hypochlorite, or alcohols, such as, for example, ethanol.

A medical study has demonstrated that, in hospitals, compliance with regard to hand washing, simple or antiseptic, does not exceed 30% to 50% depending on the study, and that the main reasons for lack of compliance are in particular the lack of time due to workload, lack of accessibility and other practical obstacles, and tolerance of repeated washing operations. The application of hydro-alcoholic solutions by friction without rinsing to dry hands without visible signs of soiling constitutes an alternative to washing the hands with an antiseptic soap. Its characteristics, namely speed of application, absence of rinsing, and rapid drying, make it possible to overcome the reasons for non-compliance with regard to washing with an antiseptic soap.

In order for the hydro-alcoholic solutions to be easily and rapidly rubbed into the hands, they must exhibit a non-greasy texture and exhibit a balance between flow characteristics which are fluid enough to be rapidly applied and rubbed at the surface of the hands and gelled enough to avoid running at the time of application. In addition, it is preferred for the hydro-alcoholic solutions to be translucent, indeed even transparent, because this aspect is associated with the notion of purity by users and consumers.

Consequently, the preparation of a disinfecting hydro-alcoholic solution faces the multifold problem consisting in making available a hydro-alcoholic solution which is homogeneous and stable over time, being characterized by an appropriate level of viscosity for the type of container and by a translucent or transparent appearance.

Synthetic polymers and polymers of natural origins are thickening agents for cosmetic aqueous phases which are well known to a person skilled in the art and which make it possible to prepare an aqueous gel for topical uses in the cosmetic and pharmaceutical fields.

The synthetic thickening polymers currently used in this field are provided in powder form or in liquid form as a water-in-oil emulsion of the polymer prepared by radical polymerization of hydrophilic monomers, in inverse emulsion, using surface-active agents, said inverse emulsion being commonly called inverse latex.

Mention may be made, among the synthetic thickening polymers in powder form which are the best known, of polymers based on acrylic acid and/or on its esters, such as those sold under the Carbopol™ or Pemulen™ names. They are described in particular in the U.S. Pat. Nos. 5,373,044 and 2,798,053 and also in the European patent application EP 0 301 532 A2. There are also polymers based on 2-acrylamido-2-methylpropanesulfonic acid and/or on its salts, such as those sold under the name Aristoflex™. They are described in particular in the European patents EP 0 816 403, EP 1 116 733 and EP 1 069 142. These powders are generally obtained by precipitating polymerization of the monomer(s) in solution in an organic solvent of benzene, ethyl acetate, cyclohexane or tert-butanol type; this process thus requires numerous successive stages of purification of the final product, in order to remove any trace of residual solvent.

There also exist synthetic thickeners exhibiting more general-purpose possibilities of use, in particular as a result of the absence of any oil phase which can result in lighter-colored aqueous gels. They are in the form of powders but have dissolution times, and thus an ease of use, comparable to those of products existing in the form of liquids. They are described in the European patent application published under the number EP 1 496 081 A2. They are obtained by conventional polymerization techniques, such as dispersed-phase radical polymerization, inverse suspension radical polymerization, combined inverse emulsion or inverse microemulsion radical polymerization, followed by separation by various techniques, such as precipitation from a third solvent, precipitation from a third solvent then optionally by washing, by drying by atomization or by azeotropic dehydration, optionally followed by washing with an astutely chosen solvent. These synthetic thickeners thus combine some of the advantages of the synthetic thickeners which are provided in the form of conventional powders (absence of oil, production of lighter-colored aqueous gels) and the advantages of the synthetic thickeners which are provided in the form of an inverse latex (preneutralization, high rate of dissolution, thickening power and stabilizing properties which are noteworthy). However, for uses intended to prepare hydro-alcoholic solutions as described above, the customers who use such synthetic thickening systems wish to be able to manufacture even clearer solutions than those obtained today.

Linear, branched or crosslinked terpolymers of at least one monomer having a free strong acid, partially salified or completely salified function, and at least one monomer of formula (A):

(A)

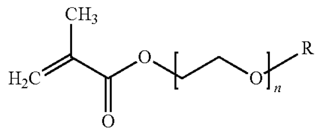

in which R represents a linear or branched alkyl radical comprising from 8 to 20 carbon atoms and n represents a number greater than or equal to 1 and less than or equal to 30, are described in the international application published under the number WO 2011/030044 and constitute good thickening agents for preparing hydro-alcoholic solutions which are stable, transparent and homogeneous overtime.

However, the joint use of a powder and alcohols to prepare hydro-alcoholic solutions requires placing each item of equipment used in a safe place, resulting in a high industrial capital cost, or, if not, resulting in low productivity and in a cost price being obtained which is inappropriate for the market concerned.

Thickeners provided in a liquid form thus appear as a solution for overcoming the abovementioned technical and economic difficulties.

Inverse latexes prepared by radical polymerization in inverse emulsion, stabilized using surface-active agents, and provided in a liquid form constitute a solution.

Mention may be made, among the inverse latexes which are the best known, of those sold under the Sepigel™, Simulgel™ and Sepiplus™ names. These thickeners are obtained by inverse emulsion radical polymerization. They can be more readily handled, in particular at ambient temperature, and disperse very rapidly in water. Furthermore, they develop remarkably elevated thickening performance qualities. However, as they contain an oil, this makes them potentially less relevant for preparing translucent or transparent aqueous gels. The United States patent published under the number U.S. Pat. No. 4,956,170 discloses hydro-alcoholic gels suitable for antimicrobial use, comprising ethanol or isopropanol, a thickening agent which is a polyacrylic acid in powder form neutralized by an amino alcohol, a hydrocarbon emollient, an emollient of fatty acid ester type, a stabilizing surfactant preventing the phase separation between the water and the alcohol, such as, for example, ethoxylated fatty alcohols, ethoxylated alkylphenols, fatty mono- and diesters of ethylene glycol, ethoxylated sorbitan esters.

SUMMARY OF THE INVENTION

The inventors have thus sought to develop novel, stable on storage, hydro-alcoholic compositions which are characterized by a dynamic viscosity, measured with a viscometer of Brookfield LVT type, of greater than or equal to 1500 mPa·s and less than or equal to 10 000 mPa·s, in order to be packaged in a bottle provided with a pump device, and which exhibits a transparent appearance.

The term "transparent appearance" is understood to mean, within the meaning of the present invention, a visual aspect of the appearance of said hydro-alcoholic composition, which is reflected by a value being obtained for the haze of said composition which is less than or equal to 25 NTU, measured at a temperature of 25° C. and using an optical turbidimeter of DRT 100B model sold by HF Scientific, precalibrated with a solution of formazine (0.9 NTU).

A solution according to the invention is a composition ($C_1$) for hand disinfection comprising:

a) at least one alcohol containing from 1 to 4 carbon atoms, b) at least one emulsion (ε) of water-in-oil type comprising:

a crosslinked anionic polyelectrolyte (P);

a fatty phase consisting of at least one oil (0), water, an emulsifying system of water-in-oil type ($S_1$), and an emulsifying system of oil-in-water type ($S_2$);

c) at least one compound of formula (II):

$$R_2—(C{=}O)—O—(CH_2—CH_2—O)_x—CH_2—CH[(O—CH_2—CH_2)_y—O—(C{=}O)—R_3]—CH_2—(O—CH_2—CH_2)_z—O—(C{=}O)—R_4 \quad (II)$$

in which $R_2—(C{=}O)$, $R_3—(C{=}O)$ and $R_4—(C{=}O)$, which are identical or different, represent a saturated or unsaturated, linear or branched, acyl group comprising from 16 to 24 carbon atoms and in which the sum x+y+z is greater than or equal to 30 and less than or equal to 100; and d) water.

As the case may be, the composition according to the invention can exhibit one or more of the characteristics below:

the emulsion (ε) of water-in-oil type comprises, per 100% of its weight: from 10% to 90% by weight of the crosslinked anionic polyelectrolyte (P), from 5% to 50% by weight of the fatty phase consisting of at least one oil (0), from 1% to 50% by weight of water, from 0.5% to 10% by weight of the emulsifying system of water-in-oil type ($S_1$) and from 2% to 10% by weight of the emulsifying system of oil-in-water type ($S_2$); the sum of the proportions by weight of compounds being equal to 100% by weight.

The composition ($C_1$) comprises:

a) from 55% to 85% by weight of alcohol comprising from 1 to 4 carbon atoms, b) from 0.5% to 3% by weight of the emulsion (ε), c) from 0.5% to 5% by weight of the compound of formula (II), d) from 14% to 37% by weight of water.

the alcohol is of formula (I)

$$R_1—OH \quad (I)$$

in which $R_1$ represents a radical included among the elements of the group consisting of the methyl, ethyl, 1-propyl and 2-propyl radicals. Preferably, the ethyl and 2-propyl radicals will be chosen.

the alcohol of formula (I) is ethanol. Ethanol is known for its speed of action, its power of rapid evaporation and its activity on bacteria and on fungi, and proves to be more active on viruses than povidone or chlorhexidine used for antiseptic washes.

The composition ($C_1$) comprises an emollient and/or moisturizing agent.

the emollient and/or moisturizing agent is chosen from the elements of the group consisting of urea, lactic acid, hydroxyurea, triethanolamine, propane-1,2-diol, sorbitol, xylitol, erythritol, glycerol, the compound of formula (III)

$$HO—[CH_2—CH(OH)—CH_2—O]_p—H \quad (III),$$

in which formula (III) p represents an integer greater than or equal to 2 and less than or equal to 6, the composition ($C_A$) represented by the formula (IV):

$$HO—CH_2—(CHOH)_m—CH_2—O\text{-}(G)_x\text{-}H \quad (IV),$$

in which formula (IV) G represents the residue of a reducing sugar, m represents an integer equal to 2, 3 or 4 and x, which indicates the mean degree of polymerization of said residue G, represents a decimal number greater than 1 and less than or equal to 5.

the said residue G of a reducing sugar is chosen from the residues of glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose, preferably said residue G of a reducing sugar is chosen from the residues of glucose, xylose and arabinose and more preferentially still G represents the residue of glucose in the formula (IV).

G represents the glucosyl or α,β-D-glucopyranosyl radical, obtained from the deletion of the hemiacetal hydroxyl group of α,β-D-glucopyranose, or the xylosyl or α,β-D-xylopyranosyl radical, obtained from the deletion of the hemiacetal hydroxyl group of α,β-D-xylopyranose in the formula (IV).

said composition ($C_A$) consists essentially of a mixture of compounds represented by the formulas ($IV_1$), ($IV_2$), ($IV_3$), ($IV_4$) and ($IV_5$):

$$HO—CH_2—(CHOH)_m—CH_2—O\text{-}(G)_1\text{-}H \quad (IV_1),$$

$$HO—CH_2—(CHOH)_m—CH_2—O\text{-}(G)_2\text{-}H \quad (IV_2),$$

$$HO—CH_2—(CHOH)_m—CH_2—O\text{-}(G)_3\text{-}H \quad (IV_3),$$

$$HO—CH_2—(CHOH)_m—CH_2—O\text{-}(G)_4\text{-}H \quad (IV_4),$$

$$HO—CH_2—(CHOH)_m—CH_2—O\text{-}(G)_5\text{-}H \quad (IV_5),$$

in the respective molar proportions $a_1$, $a_2$, $a_3$, $a_4$ and as, such that the sum $a_1+a_2+a_3+a_4+a_5$ is equal to 1 and that the sum $a_1+2a_2+3a_3+4a_4+5a_5$ is equal to x.

In the preceding definition, the term "essentially" indicates that the presence of one or more compounds of formula ($IV_w$) with w greater than 5 is not excluded within the composition ($C_A$) but that, if it is present, it is present in minimal proportions which do not result in any substantial modification of the properties of said composition ($C_A$).

In the formula (IV) as defined above, the $HO—CH_2—(CHOH)_m—CH_2—O—$ group is bonded to $(G)_x$ by the anomeric carbon of the saccharide residue, so as to form an acetal function.

In the formula (IV), x represents a decimal number greater than or equal to 1.05 and less than or equal to 3 and very particularly greater than or equal to 1.15 and less than or equal to 2.5.

in the formula (IV), m is equal to 2 or to 3 or to 4, the emollient and/or moisturizing agent is glycerol, the concentration of emollient and/or moisturizing agent is less than or equal to 5% by weight, the crosslinked anionic polyelectrolyte (P) consists of: at least one monomeric unit resulting from 2-methyl-2-[(1-oxo-2-propenyl)amino]-1-propanesulfonic acid in the free acid or partially or completely salified form; at least one monomeric unit resulting from at least one monomer chosen from the elements of the group consisting of acrylamide, N,N-dimethylacrylamide, methacrylamide, N-isopropylacrylamide, N-(tert-butyl)acrylamide, 2-hydroxyethyl acrylate, 2,3-dihydroxypropyl acrylate, 2-hydroxyethyl methacrylate, 2,3-dihydroxypropyl methacrylate, or vinylpyrrolidone; acrylic acid, methacrylic acid, 2-(carboxyethyl)acrylic acid, itaconic acid, maleic acid, 3-methyl-3-[(1-oxo-2-propenyl)amino]butanoic acid, the carboxyl function of said monomers being in free acid, partially salified or completely salified form, preferably the elements of the group consisting of acrylamide, N,N-dimethylacrylamide, methacrylamide, N-isopropylacrylamide, N-(tert-butyl)acrylamide; and at least one monomeric unit resulting from a polyethylenic crosslinking monomer (CA).

the polyethylenic crosslinking monomer (CA) is chosen from methylenebis(acrylamide), ethylene glycol dimethacrylate, diethylene glycol diacrylate, ethylene glycol diacrylate, diallylurea, triallylamine, trimethylolpropane triacrylate, diallyloxyacetic acid or one of its salts, such as sodium diallyloxyacetate, or a mixture of these compounds. Preferably, the polyethylenic crosslinking monomer (CA) is chosen from triallylamine or methylenebis(acrylamide) or a mixture of these compounds.

the crosslinked anionic polyelectrolyte (P) comprises, per 100 mol %, a proportion of greater than or equal to 20 mol % and less than or equal to 100 mol % of monomeric units resulting from 2-methyl-2-[(1-oxo-2-propenyl)amino]-1-propanesulfonic acid in free acid or partially or completely salified form.

the crosslinked anionic polyelectrolyte (P) comprises, per 100 mol %: between 20% and 90% of the monomeric unit resulting from 2-methyl-2-[(1-oxo-2-propenyl)amino]-1-propanesulfonic acid in free acid or partially or completely salified form; between 10% and 80% of the monomeric unit resulting from at least one monomer chosen from the elements of the group consisting of acrylamide, N,N-dimethylacrylamide, 2-hydroxyethyl acrylate, acrylic acid, methacrylic acid and 2-(carboxyethyl)acrylic acid, and a proportion of greater than 0 mol % and less than or equal to 1 mol % of monomeric units resulting from at least one polyethylenic crosslinking monomer (CA) chosen from methylenebis(acrylamide) and triallylamine, the crosslinked anionic polyelectrolyte (P) comprises at least one monomeric unit resulting from 2-methyl-2-[(1-oxo-2-propenyl)amino]-1-propanesulfonic acid in free acid or partially or completely salified form and at least one monomeric unit resulting from a polyethylenic crosslinking monomer (CA). The term "salified" indicates that the acid function present in a monomer exists in an anionic form combined in the salt form with a cation, in particular salts of alkali metals, such as sodium or potassium cations, or such as cations of nitrogenous bases, such as the ammonium salt, the lysine salt or the monoethanolamine salt ($HO—CH_2—CH_2—NH_3^+$). They are preferably sodium or ammonium salts.

the oil (O) is chosen from the elements of the group consisting of undecane, tridecane, isododecane, isohexadecane, the $C_{13-14}$ isoparaffins mixture, squalane, hydrogenated polyisobutene or hydrogenated polydecene.

the emulsifying system ($S_1$) of water-in-oil type comprises at least one element of the group consisting of sorbitan laurate, sorbitan palmitate, sorbitan stearate, sorbitan oleate, sorbitan sesquioleate, sorbitan trioleate, sorbitan isolaurate, sorbitan isostearate, oleoylalkanolamide, PEG-30 dipolyhydroxystearate and trimethylolpropane-30 tripolyhydroxystearate.

the emulsifying system ($S_2$) of oil-in-water type comprises at least one element of the group consisting of sorbitan oleate polyethoxylated with 20 mol of ethylene oxide, sorbitan laurate polyethoxylated with 20 mol of ethylene oxide, sorbitan palmitate polyethoxylated with 20 mol of ethylene oxide, sorbitan stearate polyethoxylated with 20 mol of ethylene oxide, tridecyl alcohol polyethoxylated with 6 mol of ethylene oxide, lauryl alcohol polyethoxylated with 7 mol of ethylene oxide, alkylpolyglycosides, compositions of fatty alcohols and of alkylpolyglycosides, polyglycerol esters, and compositions of polyglycerol esters and of polyglycerol.

the emulsifying system ($S_2$) of oil-in-water type consists either of a single emulsifying surfactant or of a mixture of emulsifying surfactants, provided that said resulting emulsifying system ($S_2$) has an HLB ("Hydrophilic-Lipophilic Balance") value high enough, generally of greater than 9 and less than or equal to 16, to induce the formation of stable emulsions of oil-in-water type.

the emulsion (ε) of water-in-oil type comprises, per 100% of its own weight:

i) from 10% by weight to 90% by weight of a crosslinked anionic polyelectrolyte (P) comprising, per 100 mol %: between 20 mol % and 90 mol % of the monomeric unit resulting from 2-methyl-2-[(1-oxo-2-propenyl)amino]-1-propanesulfonic acid in free acid or partially or completely salified form; between 10 mol % and 80 mol % of the monomeric unit resulting from acrylamide; and a proportion of greater than 0 mol % and less than or equal to 1 mol % of a monomeric unit resulting from methylenebis(acrylamide) or from triallylamine, ii) from 5% by weight to 50% by weight of a fatty phase consisting of at least one oil (0) chosen from the elements of the group consisting of isohexadecane and the $C_{13-14}$ isoparaffins mixture, iii) from 1% by weight to 50% by weight of water, iv) from 0.5% by weight to 10% by weight of an emulsifying system of water-in-oil type ($S_1$) comprising at least one element of the group consisting of sorbitan laurate, sorbitan stearate, sorbitan oleate, oleoylalkanolamide and PEG-30 dipolyhydroxystearate, and v) from 2% by weight to 10% by weight of an emulsifying system of oil-in-water type ($S_2$) comprising at least one element of the group consisting of sorbitan oleate polyethoxylated with 20 mol of ethylene oxide, sorbitan laurate polyethoxylated with 20 mol of ethylene oxide, sorbitan stearate polyethoxylated with 20 mol of ethylene oxide, tridecyl alcohol polyethoxylated with 6 mol of ethylene oxide, lauryl alcohol polyethoxylated with 7 mol of ethylene oxide, polyglyceryl-10 laurate, polyglyceryl-6 laurate, and the mixture of polyglyceryl-6 laurate and of polyglyceryl-6; the sum of the proportions by weight of compounds according to $c_1$), $c_2$), $c_3$), $c_4$) and $c_5$) being equal to 100% by weight.

in the formula (II), $R_2$—(C═O), $R_3$—(C═O) and $R_4$—(C═O) are identical or different and represent a saturated or unsaturated, linear or branched, acyl group chosen from the elements of the group consisting of the ricinoleoyl (or 12-hydroxy-9-cis-octadecenoyl), palmitoyl (or hexadecanoyl), stearoyl (or octadecanoyl), oleoyl (or (9Z)-octadecenoyl), linoleoyl (or (9Z, 12Z)-octadeca-9, 12-dienoyl), α-linolenoyl (or (9Z, 12Z, 15Z)-octadeca-9, 12, 15-trienoyl) and 9, 10-dihydroxyoctadecanoyl (or 9, 10-dihydroxystearoyl) radicals, or their mixture.

The sum x+y+z is greater than or equal to 30 and less than or equal to 50.

The compounds of formula (II) are chosen from hydrogenated castor oils polyethoxylated with between 30 and 100 mol of ethylene oxide, such as, for example, hydrogenated castor oil ethoxylated with 30 mol of ethylene oxide, hydrogenated castor oil ethoxylated with 40 mol of ethylene oxide or hydrogenated castor oil ethoxylated with 50 mol of ethylene oxide.

The composition ($C_1$) comprises, per 100% of its weight:

i) from 55% to 85% of ethanol ii) from 0% to 5% by weight of glycerol iii) from 0.5% to 3% by weight of at least one emulsion (ε) of water-in-oil type comprising, per 100% of its own weight:

from 10% by weight to 90% by weight of a crosslinked anionic polyelectrolyte (P) comprising, per 100 mol %: between 20 mol % and 90 mol % of the monomeric unit resulting from 2-methyl-2-[(1-oxo-2-propenyl)amino]-1-propanesulfonic acid in free acid or partially or completely salified form; between 10 mol % and 80 mol % of the monomeric unit resulting from acrylamide; and a proportion of greater than 0 mol % and less than or equal to 1 mol % of a monomeric unit resulting from methylenebis(acrylamide) or from triallylamine, from 5% by weight to 50% by weight of a fatty phase consisting of at least one oil (O) chosen from the elements of the group consisting of isohexadecane and the $C_{13-14}$ isoparaffins mixture, from 1% by weight to 50% by weight of water, from 0.5% by weight to 10% by weight of an emulsifying system of water-in-oil type ($S_1$) comprising at least one element of the group consisting of sorbitan oleate, oleoylalkanolamide and PEG-30 dipolyhydroxystearate, and from 2% by weight to 10% by weight of an emulsifying system of oil-in-water type ($S_2$) comprising at least one element of the group consisting of sorbitan oleate polyethoxylated with 20 mol of ethylene oxide, sorbitan laurate polyethoxylated with 20 mol of ethylene oxide, sorbitan stearate polyethoxylated with 20 mol of ethylene oxide, tridecyl alcohol polyethoxylated with 6 mol of ethylene oxide, lauryl alcohol polyethoxylated with 7 mol of ethylene oxide, polyglyceryl-10 laurate, polyglyceryl-6 laurate, and the mixture of polyglyceryl-6 laurate and of polyglyceryl-6;

the sum of the proportions by weight of these four compounds being equal to 100% by weight, iv) from 0.5% to 5% by weight of at least one compound of formula (II) which is a castor oil polyethoxylated with 40 mol of ethylene oxide.

The term "emollient agent" is understood to mean, within the meaning of the present patent application, compounds which, brought into contact with the skin, are characterized by their ability to fill in the intercellular spaces existing between the corneocytes (cells of the horny layer of the epidermis); they also limit the evaporation of water from the epidermis but to a lesser extent than occlusive agents.

The term "moisturizing agent" is understood to mean, within the meaning of the present patent application, a compound which has a "moisturizing effect" when it is brought into contact with the skin.

The term "moisturizing effect" is understood to mean, within the meaning of the present patent application, an increase in the degree of moisturization of the stratum corneum resulting from the topical application of a chemical substance or of a chemical composition to the surface of the skin to be treated.

Compound of formula (III) as defined above denotes diglycerol when p is equal to 2, triglycerol when p is equal to 3, tetraglycerol when p is equal to 4, pentaglycerol when p is equal to 5 and hexaglycerol when p is equal to 6.

Reducing sugar denotes, in the formula (IV) as defined above, the saccharide derivatives which do not exhibit, in their structures, a glycoside bond established between an anomeric carbon and the oxygen of an acetal group, as are defined in the reference publication: "Biochemistry", Daniel Voet/Judith G. Voet, p. 250, John Wiley & Sons, 1990. The oligomeric structure $(G)_x$ can exist in all forms of isomerisms, whether it is optical isomerism, geometrical isomerism or positional isomerism; it can also represent a mixture of isomers.

Crosslinked anionic polyelectrolyte (P) denotes, in the definition of the emulsion of water-in-oil type (ε) present in the composition ($C_1$) which is a subject matter of the present invention, a nonlinear crosslinked anionic polyelectrolyte which exists in the state of a three-dimensional network which is insoluble in water but swellable in water and which results in a chemical gel being obtained.

According to another specific aspect of the present invention, said crosslinked anionic polyelectrolyte (P) is an element of the group consisting of a homopolymer of 2-methyl-2-[(1-oxo-2-propenyl)amino]-1-propanesulfonic acid partially or completely salified in sodium salt or ammonium salt form, crosslinked by triallylamine and/or methylenebis(acrylamide); a copolymer of 2-methyl-2-[(1-oxo-2-propenyl)amino]-1-propanesulfonic acid partially or completely salified in sodium salt or ammonium salt form and of acrylic acid partially or completely salified in sodium salt or ammonium salt form, crosslinked by triallylamine and/or methylenebis(acrylamide); a copolymer of 2-methyl-2-[(1-oxo-2-propenyl)amino]-1-propanesulfonic acid (γ) partially or completely salified in sodium salt or ammonium salt form and of acrylic acid (6) partially or completely salified in sodium salt form in a molar ratio (γ)/(δ) of greater than or equal to 30/70 and less than or equal to 90/10, crosslinked by triallylamine and/or methylenebis(acrylamide); a copolymer of 2-methyl-2-[(1-oxo-2-propenyl)amino]-1-propanesulfonic acid (γ) partially or completely salified in sodium salt form and of acrylic acid (δ) partially or completely salified in sodium salt form in a molar ratio (γ)/(δ) of greater than or equal to 40/60 and less than or equal to 90/10, crosslinked by triallylamine and/or methylenebis(acrylamide); a copolymer of 2-methyl-2-[(1-oxo-2-propenyl)amino]-1-propanesulfonic acid (γ) partially or completely salified in sodium salt form and of acrylamide (ε) in a molar ratio (γ)/(ε) of greater than or equal to 30/70 and less than or equal to 90/10, crosslinked by triallylamine and/or methylenebis(acrylamide); a copolymer of 2-methyl-2-[(1-oxo-2-propenyl)amino]-1-propanesulfonic acid (γ) partially or completely salified in sodium salt form and of hydroxyethyl acrylate (ξ) in a molar ratio (γ)/(ξ) of greater than or equal to 30/70 and less than or equal to 90/10, crosslinked by triallylamine and/or methylenebis(acrylamide); a terpolymer of 2-methyl-2-[(1-oxo-2-propenyl)amino]-1-propanesulfonic acid partially or completely salified in sodium salt or ammonium salt form, of acrylamide and of acrylic acid partially or completely salified in sodium salt or ammonium salt form, crosslinked by triallylamine and/or methylenebis(acrylamide); a terpolymer crosslinked by triallylamine and/or methylenebis(acrylamide) of 2-methyl-2-[(1-oxo-2-propenyl)amino]-1-propanesulfonic acid partially or completely salified in sodium salt or ammonium salt form in a molar proportion of greater than or equal to 30% and less than or equal to 45%, of acrylamide in a molar proportion of greater than or equal to 45% and less than or equal to 68% and of acrylic acid partially or completely salified in sodium salt or ammonium salt form in a molar proportion of greater than or equal to 2% and less than or equal to 10%; a terpolymer crosslinked by triallylamine and/or methylenebis(acrylamide) of 2-methyl-2-[(1-oxo-2-propenyl)amino]-1-propanesulfonic acid partially or completely salified in sodium salt or ammonium salt form in a molar proportion of greater than or equal to 30% and less than or equal to 45%, of acrylamide in a molar proportion of greater than or equal to 47% and less than or equal to 68% and of acrylic acid partially or completely salified in sodium salt or ammonium salt form in a molar proportion of greater than or equal to 2% and less than or equal to 8%.

Oil (O) denotes, in the definition of the emulsion (ε) present in the composition ($C_1$) which is a subject matter of the present invention, in particular:

- linear alkanes comprising from 11 to 19 carbon atoms;
- branched alkanes comprising from 7 to 40 carbon atoms, such as isododecane, isopentadecane, isohexadecane, isoheptadecane, isooctadecane, isononadecane or isoeicosane, or mixtures of some of them, such as those mentioned below and identified by their INCI names: $C_{7-8}$ isoparaffin, $C_{8-9}$ isoparaffin, $C_{9-11}$ isoparaffin, $C_{9-12}$ isoparaffin, $C_9$-13 isoparaffin, $C_{9-14}$ isoparaffin, $C_{9-16}$ isoparaffin, isoparaffin, $C_{10-12}$ isoparaffin, $C_{10-13}$ isoparaffin, $C_{11-12}$ isoparaffin, $C_{11-13}$ isoparaffin, $C_{11-14}$ isoparaffin, $C_{12-14}$ isoparaffin, $C_{12-20}$ isoparaffin, $C_{13-14}$ isoparaffin, $C_{13-16}$ isoparaffin;
- cycloalkanes optionally substituted by one or more linear or branched alkyl radicals;
- white mineral oils, such as those sold under the following names: Marcol™ 52, Marcol™ 82, Drakeol™ 6VR, Eolane™ 130, Eolane™ 150;
- hemisqualane (or 2,6,10-trimethyldodecane; CAS number: 3891-98-3), squalane (or 2,6,10,15,19,23-hexamethyltetracosane), hydrogenated polyisobutene or hydrogenated polydecene;
- mixtures of alkanes comprising from 15 to 19 carbon atoms, said alkanes being linear alkanes, branched alkanes and cycloalkanes, and more particularly the mixture ($M_1$) which comprises, per 100% of its weight, a proportion by weight of branched alkanes of greater than or equal to 90% and less than or equal to 100%; a proportion by weight of linear alkanes of greater than or equal to 0% and less than or equal to 9%, and more particularly of less than 5%, and a proportion by weight of cycloalkanes of greater than or equal to 0% and of less than or equal to 1%, for example the mixtures sold under the name Emogreen™ L15 or Emogreen™ L19;
- fatty alcohol ethers of formula (V):

$$Z_1—O—Z_2 \quad (V),$$

in which $Z_1$ and $Z_2$, which are identical or different, represent a linear or branched alkyl radical comprising from 5 to 18 carbon atoms, for example dioctyl ether, didecyl ether, didodecyl ether, dodecyl octyl ether, dihexadecyl ether, 1,3-dimethylbutyl tetradecyl ether, 1,3-dimethylbutyl hexadecyl ether, bis(1,3-dimethylbutyl) ether or dihexyl ether;

monoesters of fatty acids and of alcohols of formula (VI):

$$R'_1\text{—(C═O)—O—}R'_2 \qquad \text{(VI),}$$

in which $R'_1$—(C═O) represents a saturated or unsaturated, linear or branched, acyl radical comprising from 8 to 24 carbon atoms and R'2 represents, independently of $R'_1$, a saturated or unsaturated, linear or branched, hydrocarbon chain comprising from 1 to 24 carbon atoms, for example methyl laurate, ethyl laurate, propyl laurate, isopropyl laurate, butyl laurate, 2-butyl laurate, hexyl laurate, methyl cocoate, ethyl cocoate, propyl cocoate, isopropyl cocoate, butyl cocoate, 2-butyl cocoate, hexyl cocoate, methyl myristate, ethyl myristate, propyl myristate, isopropyl myristate, butyl myristate, 2-butyl myristate, hexyl myristate, octyl myristate, methyl palmitate, ethyl palmitate, propyl palmitate, isopropyl palmitate, butyl palmitate, 2-butyl palmitate, hexyl palmitate, octyl palmitate, methyl oleate, ethyl oleate, propyl oleate, isopropyl oleate, butyl oleate, 2-butyl oleate, hexyl oleate, octyl oleate, methyl stearate, ethyl stearate, propyl stearate, isopropyl stearate, butyl stearate, 2-butyl stearate, hexyl stearate, octyl stearate, methyl isostearate, ethyl isostearate, propyl isostearate, isopropyl isostearate, butyl isostearate, 2-butyl isostearate, hexyl isostearate or isostearyl isostearate;

diesters of fatty acids and of glycerol of formula (VII) and of formula (VIII):

$$R'_3\text{—(C═O)—O—}CH_2\text{—CH(OH)—}CH_2\text{—O—(C═O)—}R'_4 \qquad \text{(VII)}$$

$$R'_5\text{—(C═O)—O—}CH_2\text{—CH[O—(C═O)—}R'_6\text{]—}CH_2\text{—OH} \qquad \text{(VIII),}$$

in which formulae (VII) and (VIII) $R'_3$—(C═O), $R'_4$—(C═O), $R'_5$—(C═O) and $R'_6$—(C═O), which are identical or different, represent a saturated or unsaturated, linear or branched, acyl group comprising from 8 to 24 carbon atoms;

triesters of fatty acids and of glycerol of formula (IX):

$$R'_7\text{—(C═O)—O—}CH_2\text{—CH[O—(C═O)—}R''_8\text{]—}CH_2\text{—O—(C═O)—}R''_9 \qquad \text{(IX),}$$

in which $R'_7$—(C═O), $R'_8$—(C═O) and $R'_9$—(C═O), which are identical or different, represent a saturated or unsaturated, linear or branched, acyl group comprising from 8 to 24 carbon atoms.

According to another specific aspect of the present invention, said oil (O) is chosen from undecane, tridecane, isododecane or isohexadecane, mixtures of isoparaffins, such as $C_{11-13}$ isoparaffins mixture, $C_{11-14}$ isoparaffins mixture, $C_{12-14}$ isoparaffins mixture, $C_{13-14}$ isoparaffins mixture or the mixture sold under the trade name Isopar™ M, $C_{13-16}$ isoparaffins, mixtures of alkanes and isoalkanes and cycloalkanes, such as the mixture ($M_1$) as defined above and the mixtures sold under the name Emogreen™ L15, Emogreen™ L19, Emosmart™ L15, Emosmart™ L19 or Emosmart™ V21; the white mineral oils sold under the name Marcol™ 52, Marcol™ 82, Drakeol™ 6VR, Eolane™ 130 or Eolane™ 150; hemisqualane, squalane, hydrogenated polyisobutene or hydrogenated polydecene; dioctyl ether or didecyl ether; isopropyl myristate, hexyl palmitate, octyl palmitate, isostearyl isostearate, octanoyl/decanoyl triglyceride, hexadecanoyl/octadecanoyl triglyceride or the triglycerides resulting from rapeseed oil, sunflower oil, linseed oil or palm oil.

In said emulsion (ε) present in the composition ($C_1$) which is a subject matter of the present invention, the emulsifying system ($S_1$) of water-in-oil type consists either of a single emulsifying surfactant or of a mixture of emulsifying surfactants, provided that said resulting emulsifying system ($S_1$) has a sufficiently low HLB (Hydrophilic-Lipophilic Balance) value to bring about the formation of emulsions of water-in-oil type.

Examples of emulsifying surfactant present in the system ($S_1$) of water-in-oil type include esters of anhydrohexitol and of saturated or unsaturated, linear or branched, aliphatic carboxylic acids comprising from 12 to 22 carbon atoms, optionally substituted with one or more hydroxyl groups, and more particularly esters of anhydrohexitol chosen from anhydrosorbitols and anhydromannitols and of saturated or unsaturated, linear or branched, aliphatic carboxylic acids comprising from 12 to 22 carbon atoms, optionally substituted with one or more hydroxyl groups.

According to another specific aspect of the present invention, the at least one surfactant present in said emulsifying system ($S_1$) of water-in-oil type is chosen from the elements of the group consisting of sorbitan laurate, for example that sold under the name Montane™ 20, sorbitan palmitate, for example that sold under the name Montane™ 40, sorbitan stearate, for example that sold under the name Montane™ 60, sorbitan oleate, for example that sold under the name Montane™ 80, sorbitan sesquioleate, for example that sold under the name Montane™ 85, sorbitan trioleate, for example that sold under the name Montane™ 83, sorbitan isolaurate, sorbitan isostearate, for example that sold under the name Montane™ 70, mannitan laurate, mannitan oleate, or a mixture of these esters; oleoylalkanolamide; polyesters with a molecular weight of between 1000 and 3000 and resulting from the condensation between a poly(isobutenyl) succinic acid or its anhydride, such as Hypermer™ 2296, or the mixture sold under the trade name Simaline™ IE 501 A, the polyglycol polyhydroxystearates of formula (X):

(X)

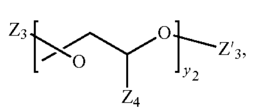

in which formula (X) $y_2$ represents an integer greater than or equal to 2 and less than or equal to 50, $Z_4$ represents a hydrogen atom, a methyl radical or an ethyl radical, $Z_3$ represents a radical of formula (XI):

(XI)

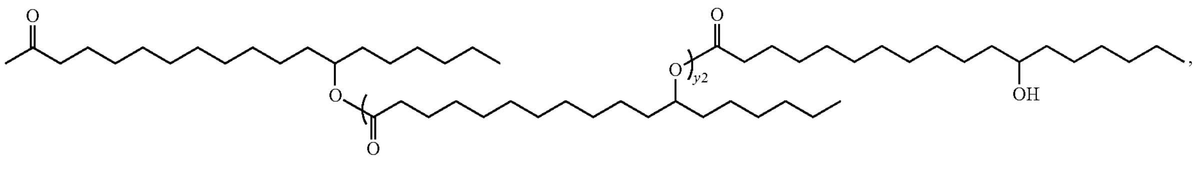

in which formula (XI) $y'_2$ represents an integer greater than or equal to 0 and less than or equal to 10, more particularly greater than or equal to 1 and less than or equal to 10, and $Z'_3$ represents a radical of formula (XI) as defined above, with $Z'_3$ identical to or different than $Z_3$, or a hydrogen atom.

Examples of emulsifying surfactant of water-in-oil type of formula (X) which can be used to prepare the emulsifying system ($S_1$) include PEG-30 dipolyhydroxystearate, sold under the name Simaline™ WO, or else the mixtures comprising PEG-30 dipolyhydroxystearate and sold under the names Simaline™ IE 201 A and Simaline™ IE 201 B, or else the mixture comprising trimethylolpropane-30 tripolyhydroxystearate sold under the name Simaline™ IE 301 B.

Mention may be made, among these constituent surface-active agents of the emulsifying system ($S_2$) of oil-in-water type, of:

- ethoxylated fatty alcohols, the aliphatic hydrocarbon chain of which comprises from 8 to 14 carbon atoms and the number of ethylene oxide units of which is of between 5 and 40, for example ethoxylated lauryl alcohol having 7 mol of ethylene oxide (INCI name: Laureth-7) or tridecyl alcohol having 6 mol of ethylene oxide (INCI name: Trideceth-6);
- ethoxylated sorbitan esters, the aliphatic hydrocarbon chain of which comprises from 12 to 22 carbon atoms and the number of ethylene oxide units of which is of between 5 and 40, for example ethoxylated sorbitan oleate having 20 mol of ethylene oxide, sold under the trade name Montanox™ 80, ethoxylated sorbitan laurate having 20 mol of ethylene oxide, sold under the trade name Montanox™ 20, sorbitan palmitate polyethoxylated with 20 mol of ethylene oxide, sold by SEPPIC under the name Montanox™ 40, or sorbitan stearate polyethoxylated with 20 mol of ethylene oxide, sold by SEPPIC under the name Montanox™ 60;
- ethoxylated alkylphenols, for example ethoxylated nonylphenols and ethoxylated octylphenols; or
- ethoxylated castor oils, for example ethoxylated castor oil having 40 mol of ethylene oxide, sold under the trade name Simulsol™ OL 50,
- polyethoxylated sorbitan hexaoleates, sold by SEPPIC under the name Simaline™ IE 400,
- polyglycerol esters and more particularly polyglycerol esters of formula (XII):

$$R''_1—(C{=}O)—[O—CH_2—CH(OH)—CH_2]_{p''}—OH \quad (XII),$$

in which:

- p" represents an integer greater than or equal to 1 and less than or equal to 15, more particularly greater than or equal to 1 and less than or equal to 10 and more particularly still greater than or equal to 4 and less than or equal to 10, and
- the $R''_1—(C{=}O)—$ group represents at least one saturated or unsaturated, linear or branched, aliphatic radical comprising from 6 to 22 carbon atoms, more particularly from 8 to 18 carbon atoms, and more particularly still the $R_1—(C{=}O)—$ group is chosen from at least one element of the group consisting of the octanoyl, decanoyl, w-undecylenoyl, dodecanoyl, tetradecanoyl, hexadecanoyl, octadecanoyl, 9-octadecenoyl or 9,12-octadecadienoyl radicals.

- mixtures of polyglycerol ester and polyglycerol, more particularly represented by a composition (Ce) which comprises, per 100% of its weight:
  - from 10% by weight to 60% by weight, more particularly from 15% by weight to 60% by weight and very particularly from 15% by weight to 50% by weight of at least one compound of formula (XIII):

$$HO—[CH_2—CH(OH)—CH_2—O]_{n''}—H \quad (XIII)$$

in which n" represents an integer greater than or equal to 1 and less than or equal to 15;

- from 40% by weight to 90% by weight, more particularly from 40% by weight to 85% by weight and very particularly from 50% by weight to 85% by weight of at least one compound of formula (XII) as defined above.

According to another even more specific aspect of the present invention, in the composition (Ce) as defined above, n" is equal to 10, p" is equal to 10 and the $R''_1—(C{=}O)—$ group is the dodecanoyl radical; n" is equal to 6, p" is equal to 10 and the $R''_1—(C{=}O)—$ group is the dodecanoyl radical; n" is equal to 6, p" is equal to 6 and the $R''_1—(C{=}O)—$ group is the dodecanoyl radical; n" is equal to 1, p" is equal to 10 and the $R_1—(C{=}O)—$ group is the dodecanoyl radical.

- alkylpolyglycosides, more particularly represented by a composition (C'2) of alkylpolyglycosides represented by the formula (XIV):

$$R_2—O\text{-}(G)_{x'}—H \quad (XIV)$$

in which x' represents a decimal number of between 1.05 and 2.5, G represents the glucosyl or α,β-D-glucopyranosyl radical, obtained from the deletion of the hemiacetal hydroxyl group of α,β-D-glucopyranose, and $R'_2$ represents a radical chosen from the elements of the group consisting of the n-octyl, n-decyl, n-dodecyl, n-tetradecyl, n-hexadecyl, n-octadecyl, n-eicosyl and n-behenyl radicals.

More particularly, $R'_2$ represents a radical chosen from the elements of the group consisting of the n-octyl, n-decyl, n-dodecyl, n-tetradecyl and n-hexadecyl radicals and x' represents a decimal number greater than or equal to 1.05 and less than or equal to 2.5, more particularly greater than or equal to 1.05 and less than or equal to 2.0 and more particularly still greater than or equal to 1.15 and less than or equal to 2.0.

- mixtures of alkylpolyglycosides and of fatty alcohols, and more particularly those represented by the combination of the composition (C'2) with a fatty alcohol of formula (XV):

$$R'_{21}—O—H \quad (XV),$$

in which $R'_{21}$, which is identical to or different from $R'_2$, represents a radical chosen from the elements of the group consisting of the n-octyl, n-decyl, n-dodecyl, n-tetradecyl, n-hexadecyl, n-octadecyl, n-eicosyl and n-behenyl radicals.

More particularly, the emulsifying agent constituting the emulsifying system of oil-in-water type ($S_2$) is a composition ($C''_2$) which comprises, per 100% of its weight:

- from 10% to 50% by weight, more particularly from 15% to 40% by weight and more particularly still from 20% to 30% by weight of at least one composition (C'2) represented by the formula (XIV) for which $R'_2$ represents at least one radical chosen from the elements of the group consisting of the n-octyl, n-decyl, n-dodecyl, n-tetradecyl and n-hexadecyl radicals, G represents the glucosyl or α,β-D-glucopyranosyl radical, obtained from the deletion of the hemiacetal hydroxyl group of α,β-D-glucopyranose, and x' represents a decimal number of greater than or equal to 1.05 and less than or equal to 2.0, from 90% to 50% by weight, more particularly from 85% to 60% by weight and more particularly still from 80% to 70% by weight of at least one fatty alcohol of formula (XV) for which $R'_{21}$, which is identical to $R'_2$, represents at least one radical chosen from the elements of the group consisting of the n-octyl, n-decyl, n-dodecyl, n-tetradecyl and n-hexadecyl radicals.

Said emulsion of water-in-oil type (ε) present in the composition ($C_1$) which is a subject matter of the present invention is prepared by carrying out an "inverse emulsion polymerization" process, which is well known to a person skilled in the art and which comprises the following stages:

- a stage a) of preparation of an aqueous phase comprising water, the water-soluble monomers and the crosslinking monomer (CA), and also commonly used additives, such as, for example, sequestering agents;
- a stage b) of mixing the oily phase (0) with the emulsifying system of water-in-oil type ($S_1$);
- a stage c) of mixing the aqueous phase and the oily phase, which are prepared during the preceding stages, and of emulsification using a stirrer of rotor-stator type;
- a stage d) of rendering inert with nitrogen;
- a stage e) of initiation of the polymerization reaction by introduction, into the emulsion formed in c), of a free-radical initiator and of optionally a coinitiator; the reaction is then allowed to take place;
- a stage f) of introduction of the emulsifying system ($S_2$) of oil-in-water type as defined above at a temperature of less than or equal to 50° C.

According to a specific aspect of the process as defined above, the polymerization reaction of stage e) is initiated by a redox pair which generates hydrogensulfite ($HSO_3^-$) ions, such as the cumene hydroperoxide/sodium metabisulfite ($Na_2S_2O_5$) pair or the cumene hydroperoxide/thionyl chloride ($SOCl_2$) pair, at a temperature of less than or equal to 10° C., accompanied, if desired, by a polymerization coinitiator, such as, for example, azobis(isobutyronitrile), and is then carried out either quasiadiabatically, up to a temperature of greater than or equal to 50° C., or by controlling the temperature.

According to another specific aspect of the process as defined above, the reaction medium resulting from stage e) is concentrated by distillation, before carrying out stage f).

According to another specific aspect of the process as defined above, the aqueous phase prepared in stage a) can comprise chain-reducing agents, intended to reduce the length of the polymeric chains formed and to increase the degree of branching on the polymer, so as to modify the rheological properties.

Mention may be made, among the chain-reducing agents suitable for the process as defined above, of methanol, isopropanol, butylene glycol, 2-mercaptoethanol, thioglycolic acid, formic acid or its salts.

According to a specific aspect of the composition ($C_1$) which is a subject matter of the present invention, $R_2$—(C═O), $R_3$—(C═O) and $R_4$—(C═O), which are identical or different, represent, in the formula (II), a saturated linear acyl group comprising from 16 to 24 carbon atoms and more particularly at least one element of the group constituted by the palmitoyl (or hexadecanoyl), stearoyl (or octadecanoyl), 12-hydroxyoctadecanoyl, 9, 10-dihydroxyoctadecanoyl (or 9, 10-dihydroxystearoyl), arachidoyl and behenoyl radicals.

Castor oil is understood to mean, within the meaning of the present invention, a composition which comprises, per 100% of its weight, a proportion by weight of at least one triglyceride of greater than or equal to 99% by weight, said triglyceride being a compound of formula (XVI):

$$R_2—C(═O)—O—CH_2—CH[O—C(═O)—R_3]—CH_2—O—C(═O)—R_4 \quad (XVI)$$

with $R_2$—C(═O)—, $R_3$—C(═O)— and $R_4$—C(═O)— identical.

According to a specific aspect, castor oil denotes, within the meaning of the present invention, a mixture which comprises, per 100% of the weight of triglycerides of formula (I): an amount by weight of between 2% and 3% by weight of a triglyceride of formula (XVI) for which the $R_2$—C(═O)—, $R_3$—C(═O)— and $R_4$—C(═O)— radicals represent the palmitoyl radical, and/or an amount by weight of between 8% and 20% of a triglyceride of formula (I) for which the $R_2$—C(═O)—, $R_3$—C(═O)— and $R_4$—C(═O)— radicals represent the stearoyl radical, and/or an amount by weight of between 80% and 95% of a triglyceride of formula (I) for which the $R_2$—C(═O)—, $R_3$—C(═O)— and $R_4$—C(═O)— radicals represent the 12-hydroxystearoyl radical, and/or an amount by weight of between 0% and 5% by weight of a triglyceride of formula (I) for which the $R_2$—C(═O)—, $R_3$—C(═O)— and $R_4$—C(═O)— radicals represent the 9, 10-dihydroxyoctadecanoyl radical.

According to another subject matter, a subject matter of the invention is a process for the preparation of the composition ($C_1$) as defined and described above, said process comprises the following stages:

- A stage a) of preparation of the emulsion (ε),
- A stage b) of addition of the emulsion (ε) to the desired amount of water, introduced beforehand into a beaker of suitable volume, at a temperature of 20° C. and with mechanical stirring at a speed of between 500 and 1000 revolutions/minute. Stirring is continued until an aqueous gel is obtained.
- A stage c) of addition of the desired amount of ethanol with the gel resulting from stage b), so as to obtain a homogeneous mixture in the form of a gel, said addition being carried out at a temperature of 20° C. and with mechanical stirring at a speed of between 500 and 1000 revolutions/minute.
- A stage d) of addition of the compound of formula (II) to the mixture resulting from stage c), at a temperature of between 20° C. and 35° C. and with mechanical stirring at a speed of between 500 and 1000 revolutions/minute.
- Optionally a stage e) of addition of at least one emollient and/or moisturizing agent as defined above with the mixture resulting from stage d), at a temperature of between 20° C. and 35° C. and with mechanical stirring at a speed of between 500 and 1000 revolutions/minute.
- According to an alternative form of the process which is a subject matter of the invention and as described above, stage b) is followed by a stage c') consisting of the addition of a mixture of the desired amount of ethanol and of the compound of formula (II), previously prepared separately, with the gel resulting from stage b); said stage c') being carried out at a temperature of between 20° C. and 35° C. and with mechanical stirring at a speed of between 500 and 1000 revolutions/minute. The optional stage e) then remains unchanged.

The emulsion (ε) can be commercially available, such as, for example, the self-invertible inverse emulsions sold under the trade names Sepigel™ 305, Simulgel™ 600, Simulgel™ EG, Simulgel™ NS, Simulgel™ INS100, Simulgel™ FL, Simulgel™ SMS 88, Sepiplus™ 400, Sepiplus™ 265 and Sepiplus™ 800.

The emulsion (ε) can also be prepared by the use of an inverse emulsion radical polymerization process, well known to a person skilled in the art and which comprises the following stages:

a') preparation of the aqueous phase by mixing water with the water-soluble monomers as described above, the crosslinking monomer, at least one sequestering agent and optionally other additives known to a person skilled in the art;

b') preparation of an organic phase comprising at least one oil (O) and an emulsifying surfactant system ($S_1$) of water-in-oil type, c') mixing the aqueous phase and the organic phase prepared in stages a') and b') and emulsifying so as to form an emulsion, d') rendering the emulsion inert with nitrogen, e') initiating the polymerization reaction by introduction, into the inerted emulsion, of a free-radical initiator, and f') introduction, into the reaction medium resulting from stage e'), of an emulsifying surfactant system ($S_2$) of oil-in-water type at a temperature of between 30° C. and 60° C.

As the case may be, the process for the preparation of the emulsion (ε) can exhibit one or more of the characteristics below:

the process comprises, between stages a') and b'), a stage of addition, to the aqueous phase prepared in stage a'), of a solution chosen from a sodium hydroxide solution, a potassium hydroxide solution, an ammonium hydroxide solution, a monoethanolamine salt solution and a lysine salt solution;

in stage e'), the radical initiator is a redox pair which generates hydrogensulfite ($HSO_3^-$) ions, such as the cumene hydroperoxide/sodium metabisulfite ($Na_2S_2O_5$) pair or the cumene hydroperoxide/thionyl chloride ($SOCl_2$) pair;

in stage e'), a polymerization coinitiator, preferably azobis (isobutyronitrile), is introduced into the inerted emulsion;

in stage a'), the pH of the aqueous phase is adjusted to between 3.0 and 7.0, more particularly between 3.5 and 6.5 and more particularly still between 4.0 and 6.5;

the reaction medium resulting from stage e') is concentrated by distillation before carrying out stage f').

Another subject matter of the present invention is a method for disinfecting the hands, characterized in that it comprises at least one step A of application, to the skin of said hands, of the composition ($C_1$) according to the invention.

In other words, a subject matter of the invention is the use of the composition ($C_1$) for disinfecting the hands by application, to the skin of said hands, of the composition ($C_1$).

The method for disinfecting the hands can additionally comprise a stage B of rubbing the hands following the implementation of stage A.

The composition ($C_1$) according to the invention can be packaged in the form of bottles, spray bottles, pump-action sprays, roll-ons or tubes and more particularly in the form of spray bottles or pump-action sprays.

Another subject matter of the invention is thus a container, preferably a bottle, comprising a spraying means and a packaging means, and containing a composition ($C_1$) according to the invention. According to a specific aspect, the spraying means included in the container which is a subject matter of the present invention is a manual pump.

The composition ($C_1$) according to the invention can thus be applied to the palm of a hand which will either be rubbed with the other hand or used to apply the composition ($C_1$) according to the invention to another part of the body, preferably to the forearm of the other hand, in order to rub it over said other part.

DESCRIPTION OF THE PREFERRED EMBODIMENTS

The following examples illustrate the invention without, however, limiting it.

I—Preparation and Evaluation of Compositions According to the Invention and of Comparative Compositions

I-1. Preparation of the Compositions According to the Invention and of the Comparative Compositions Three hydro-alcoholic compositions according to the invention, called ($F_1$) to ($F_3$), and ten comparative compositions, called ($F'_1$) to ($F'_{10}$), for which the proportions by weight of their constituents are respectively shown in tables 1 and 2 below, are prepared.

The preparation process common to these compositions is as follows:

TABLE 1

| | ($F_1$) | ($F_2$) | ($F_3$) |
|---|---|---|---|
| Water | q.s. 100% | q.s. 100% | q.s. 100% |
| 95° Ethanol | 65% | 65% | 65% |
| Simulgel ™ 600(1) | 2% | 1.6% | — |
| ($IL_1$)(2) | — | — | 1.8% |
| Glycerol | — | — | 3% |
| Simulsol ™ P23(3) | — | — | — |
| PEG-25 hydrogenated castor oil(4) | — | — | — |
| PEG-30 hydrogenated castor oil(5) | 4% | 4% | 4% |
| Montanox ™ 80(6) | — | — | — |
| Montanox ™ 20(7) | — | — | — |
| Oramix ™ CG110(8) | — | — | — |
| Sepiclear ™ G7(9) | — | — | — |

Compositions According to the Invention

TABLE 2

| | ($F'_1$) | ($F'_2$) | ($F'_3$) | ($F'_4$) | ($F'_5$) | ($F'_6$) | ($F'_7$) | ($F'_8$) | ($F'_9$) | ($F'_{10}$) |
|---|---|---|---|---|---|---|---|---|---|---|
| Water | q.s. 100% | q.s. 100% | q.s. 100% | q.s. 100% | q.s. 100% | q.s. 100% | q.s. 100% | q.s. 100% | q.s. 100% | q.s. 100% |
| 95° Ethanol | 65% | 65% | 65% | 65% | 65% | 65% | 65% | 65% | 65% | 65% |

TABLE 2-continued

| | (F'$_1$) | (F'$_2$) | (F'$_3$) | (F'$_4$) | (F'$_5$) | (F'$_6$) | (F'$_7$) | (F'$_8$) | (F'$_9$) | (F'$_{10}$) |
|---|---|---|---|---|---|---|---|---|---|---|
| Simulgel ™ 600$^{(1)}$ | 2% | 2% | 2% | — | — | — | — | — | — | — |
| ($IL_1$)$^{(2)}$ | — | — | — | 1.6% | 1.6% | 2.2% | 1.8% | 1.8% | 1.8% | 1.8% |
| Glycerol | — | — | — | 3% | 3% | 3% | 3% | 3% | 3% | 3% |
| Simulsol ™ P23$^{(3)}$ | — | 4% | — | — | — | — | — | — | — | — |
| PEG-25 hydrogenated castor oil$^{(4)}$ | — | — | 4% | — | — | — | — | — | — | — |
| PEG-30 hydrogenated castor oil$^{(5)}$ | — | — | — | — | 1% | 1% | — | — | — | — |
| Montan OX ™ 80$^{(6)}$ | — | — | — | — | — | — | 1% | — | — | — |
| Montan OX ™ 20$^{(7)}$ | — | — | — | — | — | — | — | 1% | — | — |
| Oramix ™ CG110$^{(8)}$ | — | — | — | — | — | — | — | — | 1% | — |
| Sepiclear ™ G7$^{(9)}$ | — | — | — | — | — | — | — | — | — | 1% |

Comparative Compositions (1): Simulgel™ 600 is a self-invertible inverse latex (INCI name: Acrylamide/Sodium Acryloyldimethyl Taurate Copolymer & Isohexadecane & Polysorbate 80), provided in the form of an emulsion of water-in-oil type, the polymer backbone of which comprises the acrylamide monomer and the 2-methyl-2-[(1-oxo-2-propenyl)amino]-1-propanesulfonic acid monomer in the sodium salt form and methylenebisacrylamide, in the presence of a sorbitan oleate in the water-in-oil surfactant system of the inverse emulsion.

(2) $IL_1$): is a self-invertible inverse latex, provided in the form of an emulsion of water-in-oil type, comprising an aqueous phase itself containing a polymer, the polymeric backbone of which comprises the acrylamide monomer and the 2-methyl-2-[(1-oxo-2-propenyl) amino]-1-propanesulfonic acid monomer in the sodium salt form and methylenebisacrylamide, and the oil phase of which is a $C_{13-14}$ isoparaffin, in the presence of a sorbitan oleate in the water-in-oil surfactant system of the inverse emulsion and an ethoxylated lauryl alcohol having 7 mol of ethylene oxide in the oil-in-water surfactant system of the inverse emulsion.

The emulsion KJ is prepared according to the process described above for the emulsion (ε).

(3): Simulsol™ P23 is a lauryl alcohol ethoxylated with 23 mol of ethylene oxide (MW=1198).

(4): PEG-25 hydrogenated castor oil (INCI name) is a hydrogenated and ethoxylated castor oil having 25 mols of ethylene oxide.

(5): PEG-30 hydrogenated castor oil (INCI name) is a hydrogenated and ethoxylated castor oil having 30 mol of ethylene oxide.

(6): Montanox™ 80 is an ethoxylated sorbitan monooleate having 20 mol of ethylene oxide.

(7): Montanox™ 20 is an ethoxylated sorbitan monolaurate having 20 mol of ethylene oxide (MW=1226).

(8): Oramix™ CG 110 is an aqueous composition comprising caprylyl glucoside and capryl glucoside.

(9): Sepiclear™ G7 is an aqueous composition comprising n-heptyl glucoside.

I-2. Evaluation of the Compositions According to the Invention and of the Comparative Compositions The hydro-alcoholic compositions ($F_1$) to ($F_3$) according to the invention and the comparative hydro-alcoholic compositions (F'$_1$) to (F'$_{10}$) thus prepared are subsequently stored in an insulated climatic chamber regulated at a temperature of 25° C. for 7 days. On conclusion of this period of 7 days, each hydro-alcoholic composition is evaluated by the following measurements:

Measurement of the dynamic viscosity (μ) at 25° C. using a viscometer of Brookfield LVT type at a speed of 6 revolutions/minute (S6), fitted with the appropriate spindle, after a period of storage at 25° C. for 7 days.

Measurement of the haze of the hydro-alcoholic composition obtained at a temperature of 25° C., using an optical turbidimeter of the trade name HF Scientific™, model DRT100B, precalibrated with a formazine solution (0.9 NTU); the haze measurements are expressed in NTU units.

Visual evaluation of the appearance of the hydro-alcoholic composition prepared after a period of storage at 25° C. for 7 days; the visual appearance of each hydro-alcoholic composition is noted by the experimenter and qualified as clear (CR), cloudy (CY) or cloudy-heterogeneous (CY-H), as the case may be.

The results obtained for the hydro-alcoholic compositions ($F_1$) to ($F_3$) according to the invention and the comparative hydro-alcoholic compositions (F'$_1$) to (F'$_{10}$) are given respectively in tables 3 and 4 below.

TABLE 3

| Compositions according to the invention | ($F_1$) | ($F_2$) | ($F_3$) |
|---|---|---|---|
| Visual appearance at 25° C. 7 days | (CR) | (CR) | (CR) |
| Haze (NTU) | 5 NTU | 9 NTU | <5 NTU |
| (μ) at 25° C. 7 days | 2000 mPa · s | 2600 mPa · s | 2400 mPa · s |

Evaluation of the Compositions According to the Invention

TABLE 4

| | Comparative compositions | | | | | | | | | |
|---|---|---|---|---|---|---|---|---|---|---|
| | (F'$_1$) | (F'$_2$) | (F'$_3$) | (F'$_4$) | (F'$_5$) | (F'$_6$) | (F'$_7$) | (F'$_8$) | (F'$_9$) | (F'$_{10}$) |
| Visual appearance at 25° C. 7 days | (CY) | (CY) | (CY) | (CY) | (CY) | (CY) | (CY) | (CY) | (CY) | (CY) |
| Haze (NTU) | >1000 NTU | >1000 NTU | 117 NTU | 50 NTU | 50 NTU | 825 NTU | >100 NTU | >100 NTU | 100 NTU | 100 NTU |
| (μ) at 25° C. 7 days | 2500 mPa · s | 5800 mPa · s | 2500 mPa · s | 3800 mPa · s | 3600 mPa · s | 30200 mPa · s | 2100 mPa · s | 2400 mPa · s | 2000 mPa · s | 2000 mPa · s |

Evaluation of the Comparative Compositions

I-3. Analysis of and Commentary on the Results Obtained a) The use of solubilizing agents known to a person skilled in the art, such as, for example, Polysorbate 80, Polysorbate 20, caprylyl/capryl glucoside or n-heptyl glucoside, respectively present in the comparative compositions (F'$_7$), (F'$_8$), (F'$_9$) and (F'$_{10}$), does not make it possible to achieve hydro-alcoholic compositions which are transparent, namely the measurement of the haze of which is less than 25 NTU, whereas the formula (F$_3$), also comprising 1.8% of inverse latex KJ and 3% of glycerol but also 4% by weight of a compound of formula (II) (PEG-30 hydrogenated castor oil), makes it possible to obtain a haze of less than 25 NTU.

b) Similarly, when the composition according to the invention comprises, as thickening ingredient, the emulsion (ε) (or self-invertible inverse latex) sold under the trade name Simulgel™ 600, the selection of the compound of formula (II) (PEG-30 hydrogenated castor oil), compared with the other solubilizers known to a person skilled in the art, such as, for example, PEG-30 hydrogenated castor oil or lauryl alcohol ethoxylated with 23 mol of ethylene oxide, makes it possible to obtain hydro-alcoholic compositions which are transparent, namely the measurement of the haze of which is less than 25 NTU. Thus, the hydro-alcoholic compositions (F$_1$) and (F$_2$) are characterized by a clear physical appearance, a viscosity of greater than or equal to 1500 mPa·s and less than or equal to 10 000 mPa·s, and a haze of less than 25 NTU, unlike the comparative compositions (F'$_2$) and (F'$_3$) and the comparative composition (F'$_1$), which does not contain any solubilizing agent.

The invention claimed is:

1. A composition ($C_1$) for hand disinfection comprising:

a) at least one alcohol of formula (I):

$$R_1\text{—OH} \quad (I)$$

in which $R_1$ represents the ethyl radical, b) at least one water-in-oil emulsion (E) comprising:

a crosslinked anionic polyelectrolyte (P) consisting of:

at least one monomeric unit resulting from 2-methyl-2-[(1-oxo-2-propenyl)amino]-1-propanesulfonic acid in free acid or partially or completely salified form;

at least one monomeric unit resulting from at least one monomer chosen from the elements of the group consisting of acrylamide, N,N-dimethylacrylamide, methacrylamide, N-isopropylacrylamide and N-(tert-butyl) acrylamide;

at least one monomeric unit resulting from a polyethylenic crosslinking monomer (CA);

a fatty phase consisting of at least one oil (O), water, an emulsifying system of water-in-oil ($S_1$), and an emulsifying system of oil-in-water ($S_2$);

c) at least one compound of formula (II):

$$R_2\text{—(C=O)—O—}(CH_2\text{—}CH_2\text{—O})_x\text{—}CH_2\text{—CH}[(\text{O—}CH_2\text{—}CH_2)_y\text{—O—(C=O)—}R_3]\text{—}CH_2\text{—}(\text{O—}CH_2\text{—}CH_2)_z\text{—O—(C=O)—}R_4 \quad (II)$$

in which $R_2$—(C=O), $R_3$—(C=O) and $R_4$—(C=O), which are identical or different, represent a saturated or unsaturated, linear or branched, acyl group comprising from 16 to 24 carbon atoms and in which the sum x+y+z is greater than or equal to 30 and less than or equal to 100; and d) water.

2. The composition ($C_1$) as claimed in claim 1, wherein the water-in-oil emulsion (E) comprises, per 100% of its weight:

from 10% to 90% by weight of the crosslinked anionic polyelectrolyte (P);

from 5% to 50% by weight of the fatty phase consisting of at least one oil (O);

from 1% to 50% by weight of water;

from 0.5% to 10% by weight of the emulsifying system of water-in-oil ($S_1$); and from 2% to 10% by weight of the emulsifying system of oil-in-water ($S_2$);

the sum of the proportions by weight of compounds being equal to 100% by weight.

3. The composition ($C_1$) as claimed in claim 1, comprising:

a) from 55% to 85% by weight of ethanol, b) from 0.5% to 3% by weight of the emulsion (E), c) from 0.5% to 5% by weight of the compound of formula (II), d) from 14% to 37% by weight of water.

4. The composition ($C_1$) as claimed in claim 1, further comprising an emollient and/or moisturizing agent.

5. The composition ($C_1$) as claimed in claim 4, wherein the emollient and/or moisturizing agent is chosen from the elements of the group consisting of urea, lactic acid, hydroxyurea, triethanolamine, propane-1,2-diol, sorbitol, xylitol, erythritol, glycerol, the compound of formula (III):

$$HO—[CH_2—CH(OH)—CH_2—O]_p—H \quad (III),$$

in which formula (III) p represents an integer greater than or equal to 2 and less than or equal to 6, the composition (CA) represented by the formula (IV):

$$HO—CH_2—(CHOH)_m—CH_2—O\text{-}(G)_x\text{-}H \quad (IV),$$

in which formula (IV) G represents the residue of a reducing sugar, m represents an integer equal to 2, 3 or 4 and x, which indicates the mean degree of polymerization of said residue G, represents a decimal number of greater than 1 and less than or equal to 5.

6. The composition ($C_1$) as claimed in claim 5, wherein the polyethylenic crosslinking monomer (CA) is chosen from the group consisting of methylenebis(acrylamide), ethylene glycol dimethacrylate, diethylene glycol diacrylate, ethylene glycol diacrylate, diallylurea, triallylamine, trimethylolpropane triacrylate, diallyloxyacetic acid or a salt thereof, or a mixture of these compounds.

7. The composition ($C_1$) as claimed in claim 1, wherein the crosslinked anionic polyelectrolyte (P) comprises, per 100 mol %:

between 20% and 90% of the monomeric unit resulting from 2-methyl-2-[(1-oxo-2-propenyl)amino]-1-propanesulfonic acid in free acid or partially or completely salified form;

between 10% and 80% of the monomeric unit resulting from at least one monomer chosen from the elements of the group consisting of acrylamide and N,N-dimethylacrylamide;

and a proportion of greater than 0 mol % and of less than or equal to 1 mol % of monomeric units resulting from at least one polyethylenic crosslinking monomer (CA) chosen from methylenebis(acrylamide) and triallylamine.

8. The composition ($C_1$) as claimed in claim 1, wherein the oil (O) is chosen from the elements of the group consisting of undecane, tridecane, isododecane, isohexadecane, the $C_{13-14}$ isoparaffins mixture, squalane, hydrogenated polyisobutene or hydrogenated polydecene.

9. The composition ($C_1$) as claimed in claim 1, wherein the emulsifying system ($S_1$) of water-in-oil type comprises at least one element of the group consisting of sorbitan laurate, sorbitan palmitate, sorbitan stearate, sorbitan oleate, sorbitan sesquioleate, sorbitan trioleate, sorbitan isolaurate, sorbitan isostearate, oleoylalkanolamide, PEG-30 dipolyhydroxystearate and trimethylolpropane-30 tripolyhydroxystearate.

10. The composition ($C_1$) as claimed in claim 1, wherein the emulsifying system ($S_2$) of oil-in-water type comprises at least one element of the group consisting of sorbitan oleate polyethoxylated with 20 mol of ethylene oxide, sorbitan laurate polyethoxylated with 20 mol of ethylene oxide, sorbitan palmitate polyethoxylated with 20 mol of ethylene oxide, sorbitan stearate polyethoxylated with 20 mol of ethylene oxide, tridecyl alcohol polyethoxylated with 6 mol of ethylene oxide, lauryl alcohol polyethoxylated with 7 mol of ethylene oxide, alkylpolyglycosides, compositions of fatty alcohols and of alkylpolyglycosides, polyglycerol esters, and compositions of polyglycerol esters and of polyglycerol.

11. The composition ($C_1$) as claimed in claim 1, wherein, in the formula (II), $R_2$—(C═O), $R_3$—(C═O) and $R_4$—(C═O) are identical or different and represent a saturated or unsaturated, linear or branched, acyl group chosen from the elements of the group consisting of the ricinoleoyl (or 12-hydroxy-9-cis-octadecenoyl), palmitoyl (or hexadecanoyl), stearoyl (or octadecanoyl), oleoyl (or (9Z)-octadecenoyl), linoleoyl (or (9Z, 12Z)-octadeca-9, 12-dienoyl), α-linolenoyl (or (9Z, 12Z, 15Z)-octadeca-9, 12, 15-trienoyl) and 9, 10-dihydroxyoctadecanoyl (or 9, 10-dihydroxystearoyl) radicals, or mixture thereof.

12. A method for disinfecting the hands, comprising at least one stage A of applying, to the skin of said hands, of the composition ($C_1$) as defined in claim 1.

13. The method as claimed in claim 12, further comprising a stage B of rubbing the hands following the implementation of stage A.

14. A container comprising a manual pumping means and a packaging means, and containing a composition ($C_1$) as defined in claim 1.

15. The composition ($C_1$) as claimed in claim 2, comprising:

a) from 55% to 85% by weight of ethanol, b) from 0.5% to 3% by weight of the emulsion (E), c) from 0.5% to 5% by weight of the compound of formula (II), d) from 14% to 37% by weight of water.

16. The composition ($C_1$) as claimed in claim 2, further comprising an emollient and/or moisturizing agent.

17. The composition ($C_1$) as claimed in claim 3, further comprising an emollient and/or moisturizing agent.

18. The composition ($C_1$) as claimed in claim 2, wherein the crosslinked anionic polyelectrolyte (P) comprises, per 100 mol %:

between 20% and 90% of the monomeric unit resulting from 2-methyl-2-[(1-oxo-2-propenyl)amino]-1-propanesulfonic acid in free acid or partially or completely salified form;

between 10% and 80% of the monomeric unit resulting from at least one monomer chosen from the elements of the group consisting of acrylamide and N,N-dimethylacrylamide;

and a proportion of greater than 0 mol % and of less than or equal to 1 mol % of monomeric units resulting from at least one polyethylenic crosslinking monomer (CA) chosen from methylenebis(acrylamide) and triallylamine.

19. The composition ($C_1$) as claimed in claim 3, wherein the crosslinked anionic polyelectrolyte (P) comprises, per 100 mol %:

between 20% and 90% of the monomeric unit resulting from 2-methyl-2-[(1-oxo-2-propenyl)amino]-1-propanesulfonic acid in free acid or partially or completely salified form;

between 10% and 80% of the monomeric unit resulting from at least one monomer chosen from the elements of the group consisting of acrylamide and N,N-dimethylacrylamide;

and a proportion of greater than 0 mol % and of less than or equal to 1 mol % of monomeric units resulting from at least one polyethylenic crosslinking monomer (CA) chosen from methylenebis(acrylamide) and triallylamine.

20. The composition ($C_1$) as claimed in claim 4, wherein the crosslinked anionic polyelectrolyte (P) comprises, per 100 mol %:

between 20% and 90% of the monomeric unit resulting from 2-methyl-2-[(1-oxo-2-propenyl)amino]-1-propanesulfonic acid in free acid or partially or completely salified form;

between 10% and 80% of the monomeric unit resulting from at least one monomer chosen from the elements of the group consisting of acrylamide and N,N-dimethylacrylamide;

and a proportion of greater than 0 mol % and of less than or equal to 1 mol % of monomeric units resulting from at least one polyethylenic crosslinking monomer (CA) chosen from methylenebis(acrylamide) and triallylamine.

* * * * *